United States Patent
Burckhardt et al.

(10) Patent No.: US 10,647,807 B2
(45) Date of Patent: May 12, 2020

(54) POLYALDIMINE AND CURABLE POLYURETHANE COMPOSITION

(71) Applicant: SIKA TECHNOLOGY AG, Baar (CH)

(72) Inventors: Urs Burckhardt, Zürich (CH); Andreas Kramer, Zürich (CH)

(73) Assignee: SIKA TECHNOLOGY AG, Baar (CH)

( * ) Notice: Subject to any disclaimer, the term of this patent is extended or adjusted under 35 U.S.C. 154(b) by 61 days.

(21) Appl. No.: 15/773,972

(22) PCT Filed: Dec. 20, 2016

(86) PCT No.: PCT/EP2016/081979
§ 371 (c)(1),
(2) Date: May 4, 2018

(87) PCT Pub. No.: WO2017/108827
PCT Pub. Date: Jun. 29, 2017

(65) Prior Publication Data
US 2018/0319922 A1 Nov. 8, 2018

(30) Foreign Application Priority Data

Dec. 21, 2015 (EP) .................... 15201649

(51) Int. Cl.
| | | |
|---|---|---|
| C08G 18/48 | (2006.01) | |
| C08G 18/18 | (2006.01) | |
| C08G 18/76 | (2006.01) | |
| C08G 18/32 | (2006.01) | |
| C08G 18/75 | (2006.01) | |
| C08G 18/12 | (2006.01) | |
| C08G 18/10 | (2006.01) | |
| C09D 175/04 | (2006.01) | |
| C07C 251/08 | (2006.01) | |
| C07C 251/24 | (2006.01) | |
| C09D 175/08 | (2006.01) | |
| C09J 175/08 | (2006.01) | |
| C09K 3/10 | (2006.01) | |

(52) U.S. Cl.
CPC ........ *C08G 18/1858* (2013.01); *C07C 251/08* (2013.01); *C07C 251/24* (2013.01); *C08G 18/10* (2013.01); *C08G 18/12* (2013.01); *C08G 18/3256* (2013.01); *C08G 18/4812* (2013.01); *C08G 18/4825* (2013.01); *C08G 18/4837* (2013.01); *C08G 18/751* (2013.01); *C08G 18/755* (2013.01); *C08G 18/7621* (2013.01); *C08G 18/7671* (2013.01); *C09D 175/04* (2013.01); *C09D 175/08* (2013.01); *C09J 175/08* (2013.01); *C09K 3/1021* (2013.01)

(58) Field of Classification Search
USPC ........................................ 525/398
See application file for complete search history.

(56) References Cited

U.S. PATENT DOCUMENTS

| | | | |
|---|---|---|---|
| 5,087,661 A | 2/1992 | Aoki et al. | |
| 2003/0096893 A1 | 5/2003 | Boomgaard et al. | |

FOREIGN PATENT DOCUMENTS

| | | |
|---|---|---|
| EP | 2017260 A1 | 1/2009 |
| EP | 2 857 378 A1 | 4/2015 |
| WO | 00/64860 A1 | 11/2000 |
| WO | 2004/013088 A1 | 2/2004 |
| WO | 2009/010522 A1 | 1/2009 |

OTHER PUBLICATIONS

Apr. 11, 2017 International Search Report issued in International Patent Application No. PCT/EP2016/081979.
Jun. 10, 2019 Office Action issued in Chilean Patent Application No. 201801449.
Jun. 26, 2018 International Preliminary Report on Patentability issued in International Patent Application No. PCT/EP2016/081979.
Oct. 10, 2019 Office Action issued in Colombian Patent Application No. 2018/0006625.
Sep. 30, 2019 Office Action issued in European Patent Application No. 16 822 669.4.
Mar. 5, 2020 Office Action issued in Chilean Patent Application No. 2018001449.

*Primary Examiner* — Terressa Boykin
(74) *Attorney, Agent, or Firm* — Oliff PLC

(57) ABSTRACT

A polyaldimine of the formula (I) with advantageous properties in use as latent hardener for compositions including isocyanate groups, and compositions containing the polyaldimine of the formula (I) and at least one polyisocyanate and/or at least one polyurethane polymer containing isocyanate groups. The polyaldimine of the formula (I) is odourless, pH-neutral, liquid at room temperature, has low viscosity, has little sensitivity to heat and moisture, and is stable in storage together with isocyanates. It can provide odourless single-component polyurethane compositions which have good stability in storage and which do not produce bubbles when hardened in the presence of moisture, and which cause no problematic odour emissions, giving a hardened elastic material with good mechanical properties and surprisingly little tendency towards plasticizer migration.

15 Claims, No Drawings

POLYALDIMINE AND CURABLE POLYURETHANE COMPOSITION

TECHNICAL FIELD

The invention relates to polyaldimines and polyurethanes, and to adhesives, sealants and coatings.

PRIOR ART

Curable polyurethane compositions which crosslink through reaction of isocyanate groups with hydroxyl groups and/or moisture or water are used in many industrial applications, for example as adhesives, sealants or coatings in the construction and manufacturing industries. When compositions of this kind are used at high humidity and/or elevated temperature, the curing thereof often gives rise to disruptive blisters as a result of carbon dioxide gas released, which is not dissolved or dissipated quickly enough. In order to avoid blistering, it is possible to add chemically blocked amines to the compositions, called latent hardeners, which release amino groups on contact with moisture and are crosslinked rapidly with the isocyanate groups without formation of carbon dioxide. Latent hardeners used are usually compounds having aldimine, ketimine or oxazolidine groups. However, the known latent hardeners are disadvantageous. For instance, they can trigger premature crosslinking reactions and hence lower the storage stability of the compositions and/or accelerate the curing thereof to such a degree as to result in too short an open time and hence too short a working window. Moreover, many of the known latent hardeners, on curing, lead to troublesome emissions caused by volatile, intensely odorous aldehydes or ketones which serve as blocking agents in the latent hardener and are released through hydrolysis.

WO 00/64860 describes polyurethane compositions comprising aromatic aldimines of aromatic aldehydes. These compositions are storage-stable and have a long pot life/open time. However, the curing thereof usually proceeds with significant odor and is slow and incomplete, which can lead to blister formation, tacky surfaces and/or limited stability or extensibility. Moreover, the aldimines have to be heated or dissolved to prepare the compositions since they are highly viscous or solid at room temperature.

U.S. Pat. No. 5,087,661 describes polyaldimines having an aryl group having 6 to 15 carbon atoms, and the use thereof as latent hardeners in polyurethane compositions. Some time after preparation, most of these polyaldimines are highly viscous or solid at room temperature and therefore have to be heated or dissolved for incorporation into a polyurethane composition. The compositions often have low storage stability; especially at elevated storage temperature and/or in the case of use of sterically unhindered aromatic polyisocyanates such as MDI, there can be a significant rise in viscosity even after short time, as a result of which they become unusable. When they are used, significant, long-lasting odor nuisance additionally occurs as a result of the intensely odorous aldehydes released.

WO 2004/013088 describes polyaldimines having a long-chain tertiary alkyl group containing ester groups, and the use thereof as latent hardeners in polyurethane compositions. These polyaldimines are liquid and of low viscosity, but are thermally sensitive and moisture-sensitive and very reactive. The compositions are very storage-stable and cure completely without odor, but have a comparatively short open time. Owing to limited compatibility of the long chain aldehyde released with the cured polyurethane, they additionally have a tendency to plasticizer migration, which can be manifested by bleeding, or substrate discoloration or stress-cracking in the substrate.

WO 2009/010522 describes polyaldimines having an amine-containing tertiary alkyl group, and the use thereof as latent hardeners in polyurethane compositions. These polyaldimines are likewise liquid and easily workable, but are not pH-neutral. The compositions cure in a blister-free and low-odor manner, but are not storage-stable when aromatic polyisocyanates are used and have a very short open time.

SUMMARY OF THE INVENTION

It is therefore an object of the present invention to provide latent hardeners for polyurethanes which overcome the disadvantages of the prior art.

It has been found that, surprisingly, this object is achieved by a polyaldimine of the formula (I) as described in claim 1. The polyaldimine of the formula (I) is odorless, pH-neutral, liquid or low-melting and of comparatively low viscosity at room temperature, and has low sensitivity to heat and moisture. It can thus be stored, transported, metered and worked in a simple manner. It is surprisingly inert with isocyanates, including particularly reactive, sterically unhindered aromatic isocyanates such as, in particular, MDI and adducts thereof, even at elevated temperature, and thus enables particularly storage-stable compositions. Under the influence of moisture, the polyaldimine of the formula (I) reacts relatively slowly but nevertheless completely and faultlessly with isocyanates, and the reaction can also be speeded up by means of suitable catalysts. This enables a wide range of open times. The aldehyde released in the hydrolysis is nonvolatile, odorless and colorless, and thus does not cause any emissions or odor immissions or discoloration. It surprisingly has such good compatibility in polyurethanes that it causes barely any plasticizer migration. In spite of the long-chain substituent on the aryl radical, it is compatible in polyurethanes to a similar degree to aromatic aldehydes without long-chain substituents, but these cause a distinct to strong, long-lasting odor. The low tendency to plasticizer migration is surprising. Polyaldimines having elimination products of high molecular weight are naturally particularly critical in relation to plasticizer migration after curing, since the amount used is correspondingly high owing to the high equivalent weight, and hence a large amount of aldehyde released remains in the cured material. Moreover, the long-chain hydrophobic alkyl or alkoxy substituent, especially given branched structure, would be expected to have comparatively poor compatibility in the hydrophilic polymer skeleton of polyurethanes having hydrogen bonds.

The polyaldimine of the formula (I), owing to the specific structure with the A and Z radicals, has a particularly advantageous combination of properties that have not been achieved to date in the prior art. It is usable as a latent hardener for all commercial polyisocyanates. It enables odorless polyurethane compositions with excellent storage stability and manageable working times, which cure rapidly and completely and without blistering and entirely without odor immissions. This gives rise to a blister-free material having a non-tacky surface and good strength, extensibility and durability, which does not have a tendency to problems with plasticizer migration such as bleeding, substrate discoloration or stress-cracking in the substrate.

Further aspects of the invention are the subject of further independent claims. Particularly preferred embodiments of the invention are the subject of the dependent claims.

WAYS OF EXECUTING THE INVENTION

The invention provides a polyaldimine of the formula (I)

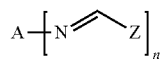

(I)

where n is 2 or 3,

Z is an aryl radical substituted by an alkyl or alkoxy group and having a total of 12 to 26 carbon atoms, and A is an n-valent aliphatic or cycloaliphatic hydrocarbyl radical optionally containing ether oxygen and having a molecular weight in the range from 42 to 6,000 g/mol, bonded via at least one tertiary or quaternary carbon atom and/or containing a bi- or tricyclic ring system.

A "tertiary carbon atom" refers to a carbon atom bonded only to one hydrogen atom.

A "quaternary carbon atom" refers to a carbon atom not bonded to any hydrogen atom.

A dotted line in the formulae in each case represents the bond between a substituent and the corresponding molecular radical.

A "primary amino group" refers to an amino group which is bonded to a single organic radical and bears two hydrogen atoms; a "secondary amino group" refers to an amino group which is bonded to two organic radicals which may also together be part of a ring and bears one hydrogen atom; and a "tertiary amino group" refers to an amino group which is bonded to three organic radicals, two or three of which may also be part of one or more rings, and does not bear any hydrogen atom.

Substance names beginning with "poly", such as polyamine, polyol or polyisocyanate, refer to substances containing, in a formal sense, two or more of the functional groups that occur in their name per molecule.

A "primary polyamine" refers to a compound having at least two primary amino groups.

An "aromatic isocyanate" refers to an isocyanate wherein the isocyanate groups are bonded directly to an aromatic carbon atom. Accordingly, isocyanate groups of this kind are referred to as "aromatic isocyanate groups". "Molecular weight" refers to the molar mass (in g/mol) of a molecule or a molecule residue. "Average molecular weight" refers to the number-average molecular weight ($M_n$) of a polydisperse mixture of oligomeric or polymeric molecules or molecule residues. It is typically determined by means of gel permeation chromatography (GPC) against polystyrene as standard.

The term "viscosity" refers to the dynamic viscosity or shear viscosity which is determined by the ratio between the shear stress and the shear rate (speed gradient) and is determined as described in DIN EN ISO 3219.

A substance or composition is referred to as "storage-stable" or "storable" when it can be stored at room temperature in a suitable container over a prolonged period, typically over at least 3 months up to 6 months or more, without any change in its application or use properties to a degree of relevance for the use thereof as a result of the storage.

"Room temperature" refers to a temperature of 23° C.

Z is preferably a radical of the formula (II)

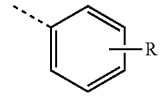

(II)

where R is a linear or branched alkyl or alkoxy radical having 6 to 20, preferably 8 to 16, carbon atoms.

R is preferably a linear or branched alkyl radical having 10 to 14 carbon atoms or a linear or branched alkoxy radical having 8 to 12 carbon atoms.

R is especially a linear or branched alkyl radical having 10 to 14 carbon atoms. A polyaldimine of this kind is particularly reactive as a latent hardener in polyurethanes.

R is more preferably a branched alkyl radical. A polyaldimine of this kind is typically liquid and of comparatively low viscosity at room temperature, which is very advantageous for handling thereof.

R is most preferably a branched alkyl radical having 10 to 14 carbon atoms. A polyaldimine of this kind is particularly reactive and is usually liquid and of comparatively low viscosity at room temperature.

Preferably, R is in the meta or para position, especially in the para position. A polyaldimine of this kind is obtainable particularly readily.

Most preferably, R is a radical of the formula

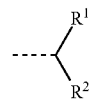

where $R^1$ and $R^2$ are each an alkyl radical and together have 9 to 13 carbon atoms. Preferably, the $R^1$ and $R^2$ radicals are each linear.

Most preferably, Z is thus a radical of the formula (IIa)

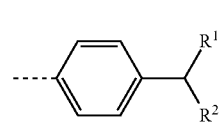

(IIa)

where $R^1$ and $R^2$ have the definitions given.

The preferred Z radicals are obtainable particularly readily and enable particularly low-odor polyaldimines which are especially liquid and particularly of low viscosity at room temperature.

A is preferably either an n-valent aliphatic or cycloaliphatic hydrocarbyl radical having a molecular weight in the range from 42 to 500 g/mol, bonded via at least one tertiary or quaternary carbon atom and/or containing a bi- or tricyclic ring system or is an n-valent polyoxyalkylene radical having a molecular weight in the range from 170 to 6,000 g/mol, preferably 170 to 2,000 g/mol, especially 170 to 470 g/mol, bonded via at least one tertiary carbon atom.

A polyaldimine of this kind is obtainable particularly easily.

More preferably, A is selected from the group consisting of 1,2-propylene, 1,3-pentylene, 2-methyl-1,5-pentylene, 2,2(4),4-trimethyl-1,6-hexamethylene, 1,2-cyclohexylene, (1,5,5-trimethylcyclohexan-1-yl)methane-1,3,4(2)-methyl- 1,3-cyclohexylene, methylenedicyclohexan-4-yl, methylenebis(2-methylcyclohexan-4-yl), (bicyclo[2.2.1]heptan-2,5 (2,6)-diyl)dimethylene, (tricyclo[5.2.1.0$^{2.6}$]decane-3(4),8 (9)-diyl)dimethylene, α,ω-polyoxypropylene having an average molecular weight in the range from 170 to 5,000 g/mol and trimethylolpropane- or glycerol-started tris(ω-polyoxypropylene) having an average molecular weight in the range from 330 to 6,000 g/mol.

The preferred A radicals are obtainable particularly readily.

Among these, preference is given to 1,2-cyclohexylene, (1,5,5-trimethylcyclohexan-1-yl)methane-1,3,4(2)-methyl-1,3-cyclohexylene, methylenedicyclohexan-4-yl, (bicyclo[2.2.1]heptane-2,5(2,6)-diyl)dimethylene, (tricyclo[5.2.1.0$^{2.6}$]decane-3(4),8(9)-diyl)dimethylene, α,ω-polyoxypropylene having an average molecular weight in the range from 170 to 470 g/mol, and trimethylolpropane- or glycerol-started tris(ω-polyoxypropylene) having an average molecular weight in the range from 330 to 450 g/mol.

These polyaldimines enable compositions having particularly good storage stability and/or particularly high strengths.

Among these, particular preference is given to (1,5,5-trimethylcyclohexan-1-yl)methane-1,3 or (bicyclo[2.2.1] heptane-2,5(2,6)-diyl)dimethylene or (tricyclo[5.2.1.0$^{2.6}$] decane-3(4),8(9)-diyl)dimethylene. These polyaldimines of the formula (I) have particularly low viscosity and enable particularly storage-stable compositions having particularly high strength.

Among these, particular preference is further given to methylenedicyclohexan-4-yl. These polyaldimines of the formula (I) enable particularly storage-stable compositions having a particularly high modulus of elasticity.

Among these, particular preference is further given to α,ω-polyoxypropylene having an average molecular weight in the range from 170 to 250 g/mol. These polyaldimines of the formula (I) have particularly low viscosity and enable particularly storage-stable compositions having particularly good extensibility. Among these, particular preference is further given to trimethylolpropane-started tris(ω-polyoxypropylene) having an average molecular weight in the range from 330 to 450 g/mol. These polyaldimines of the formula (I) have particularly low viscosity and enable particularly storage-stable compositions having particularly high crosslinking density and durability.

The preferred polyaldimines of the formula (I) are obtainable particularly readily and/or have particularly low-viscosity and/or are particularly storage-stable together with isocyanates and/or lead to particularly good mechanical properties or durabilities, and hence are particularly suitable as latent hardeners for adhesives, sealants or coatings based on polyurethane.

The polyaldimine of the formula (I) is preferably obtained from the reaction of at least one amine of the formula (III) with at least one aldehyde of the formula (IV) in a condensation reaction with release of water.

(III)

(IV)

In the formulae (III) and (IV), n, A and Z have the definitions already given.

The aldehyde of the formula (VI) is preferably used here stoichiometrically or in a stoichiometric excess in relation to the primary amino groups. In this manner, the reaction product is largely or entirely free of primary amino groups.

The invention thus further provides a reaction product comprising at least one polyaldimine of the formula (I), obtained from the reaction of at least one amine of the formula (III) with at least one aldehyde of the formula (IV) in a condensation reaction with release of water, wherein the aldehyde was present stoichiometrically or in a stoichiometric excess in relation to the primary amino groups.

The reaction is advantageously conducted at a temperature in the range from 15 to 120° C., preferably at 20 to 100° C., optionally in the presence of a solvent. The water of condensation is preferably removed from the reaction mixture, either as an azeotrope with a suitable solvent preferably directly by distillation, optionally under reduced pressure.

Optionally, a catalyst is used in the reaction, especially an acid catalyst. Particular preference is given to working without solvent and removing the water of condensation from the heated reaction mixture by means of application of reduced pressure.

A reaction product of this kind can be used without further workup as latent hardener for compositions having isocyanate groups.

Preferably, the amine of the formula (III) is combined with the aldehyde of the formula (IV) to give a reaction mixture, where the aldehyde is present stoichiometrically or in a stoichiometric excess in relation to the primary amino groups, and the water of condensation is removed from the reaction mixture by a suitable method, optionally while heating the reaction mixture.

Suitable amines of the formula (III) are primary aliphatic or cycloaliphatic di- or triamines, in which at least one primary amino group is bonded to a tertiary or quaternary carbon atom and/or which contain a bi- or tricyclic ring system.

Preferably, the amine of the formula (III) is selected from the group consisting of 1,2-propanediamine, 1,3-pentanediamine, 1,5-diamino-2-methylpentane (MPMD), 2,2(4),4-trimethyl-1,6-hexanediamine (TMD), 1,2-cyclohexanediamine, 1,3-cyclohexanediamine, 1,4-cyclohexanediamine, 1-amino-3-aminomethyl-3,5,5-trimethylcyclohexane (isophoronediamine or IPDA), 4(2)-methyl-1,3-cyclohexanediamine, bis(4-aminocyclohexyl)methane, bis(4-amino-3-methylcyclohexyl)methane, 2,5(2,6)-bis(aminomethyl) bicyclo[2.2.1]heptane (norbornanediamine or NBDA), 3(4), 8(9)-bis(aminomethyl)tricyclo[5.2.1.0$^{2.6}$]decane (TCD diamine), α,ω-polyoxypropylenediamine having an average molecular weight in the range from 200 to 4,000 g/mol, especially the Jeffamine® products D-230, D-400, XTJ-582, D-2000, XTJ-578 and D-4000 (all from Huntsman), and trimethylolpropane- or glycerol-started tris(ω-polyoxypropyleneamine) having an average molecular weight in the range from 380 to 6,000 g/mol, especially the Jeffamine® products T-403, T-3000 and T-5000 (all from Huntsman). These amines have particularly good commercial availability.

Among these, preference is given to 1,2-cyclohexanediamine, 1-amino-3-aminomethyl-3,5,5-trimethylcyclohexane (isophoronediamine or IPDA), 4(2)-methyl-1,3-cyclohexanediamine, bis(4-aminocyclohexyl)methane, 2,5(2,6)-bis(aminomethyl)bicyclo[2.2.1]heptane (norbornanediamine or NBDA), 3(4),8(9)-bis(aminomethyl)tricyclo [5.2.1.0$^{2.6}$]decane (TCD diamine), α,ω-polyoxypropylene having an average molecular weight in the range from 200 to 500 g/mol, especially Jeffamine® D-230 or Jeffamine®

D-400, or trimethylolpropane- or glycerol-started tris(ω-polyoxypropylene) having an average molecular weight in the range from 380 to 500 g/mol, especially Jeffamine® T-403.

A preferred aldehyde of the formula (IV) is an aldehyde of the formula (IVa) where R has the definitions already described.

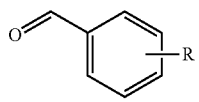

(IVa)

A particularly preferred aldehyde of the formula (IV) is an aldehyde of the formula (IVb) where $R^1$ and $R^2$ have the definitions already described.

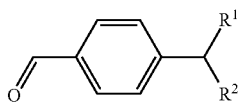

(IVb)

Especially preferred aldehydes of the formula (IV) are 4-decylbenzaldehydes, 4-undecylbenzaldehydes, 4-dodecylbenzaldehydes, 4-tridecylbenzaldehydes or 4-tetradecylbenzaldehydes, in which the alkyl radicals are linear or branched, especially branched.

A most preferred aldehyde of the formula (IV) is a mixture comprising 4-decylbenzaldehydes, 4-undecylbenzaldehydes, 4-dodecylbenzaldehydes, 4-tridecylbenzaldehydes or 4-tetradecylbenzaldehydes, the alkyl radicals of which are mainly branched.

The aldehyde of the formula (IV) is especially obtainable from the formylation of at least one alkyl- and/or alkoxy-substituted aromatic hydrocarbon with carbon monoxide under the action of an acid catalyst. An example of a suitable acid catalyst is the $HCl—AlCl_3$ system (Gattermann-Koch reaction).

In a preferred preparation process, the formylation is conducted with $HF—BF_3$ as acid catalyst. This is advantageous since this process proceeds particularly selectively and the aldehyde of the formula (IV) can be separated from the reaction mixture without a hydrolysis step and the catalyst can be reused, which means that costly and inconvenient product workup and disposal of waste is dispensed with.

The polyaldimine of the formula (I) is more preferably selected from the group consisting of N,N'-bis(4-alkylbenzylidene)-1,2-cyclohexanediamine, N,N'-bis(4-alkylbenzylidene)-3-aminomethyl-3,5,5-trimethylcyclohexylamine, N,N'-bis(4-alkylbenzylidene)-4(2)-methyl-1,3-cyclohexanediamine, N,N'-bis(4-alkylbenzylidene)-bis(4-aminocyclohexyl)methane, N,N'-bis(4-alkylbenzylidene)-2,5(2,6)-bis(aminomethyl)bicyclo[2.2.1]heptane, N,N'-bis(4-alkylbenzylidene)-3(4),8(9)-bis(aminomethyl)tricyclo[5.2.1.0$^{2.6}$]decane, N,N'-bis(4-alkylbenzylidene) polyoxypropylenediamine having an average molecular weight in the range from 650 to 1050 g/mol and N,N',N''-tris(4-alkylbenzylidene)polyoxypropylenetriamine having an average molecular weight in the range from 1050 to 1350 g/mol, where alkyl in each case is a linear or particularly branched decyl, undecyl, dodecyl, tridecyl or tetradecyl radical.

The polyaldimine of the formula (I) is odorless, pH-neutral, liquid or low-melting and of comparatively low viscosity at room temperature, and has low sensitivity to heat and moisture. It can thus be stored, transported, metered and worked in a simple manner.

Preferably, the polyaldimine of the formula (I) is a mixture of polyaldimines of the formula (I) in which each Z is a radical of the formula (II) and R is selected from alkyl radicals having 6 to 20 carbon atoms. More preferably, R is selected from linear or particularly branched decyl, undecyl, dodecyl, tridecyl and tetradecyl radicals.

The invention thus further provides a mixture of polyaldimines of the formula (I) in which each Z is a radical of the formula (II) and R is selected from linear or particularly branched decyl, undecyl, dodecyl, tridecyl and tetradecyl radicals. A mixture of this kind is industrially obtainable particularly easily.

The invention further provides for the use of at least one polyaldimine of the formula (I) as latent hardener for compositions containing isocyanate groups. The polyaldimine of the formula (I) has advantageous properties for the use described. It has excellent miscibility into compositions having isocyanate groups and shows barely any tendency to separation. It does not trigger any crosslinking reactions of the isocyanate groups in the absence of water or moisture and thus enables very good storage stability. On ingress of moisture, it reacts rapidly and completely via hydrolyzing aldimino groups with the isocyanate groups, this reaction proceeding very substantially without competing isocyanate hydrolysis and hence without blistering. And finally, the aldehyde released in the curing is nonvolatile and hydrolysis-stable, does not cause any odor nuisance, has excellent compatibility with the cured polymer and barely bleeds or migrates into the substrates.

Preferably, the composition containing isocyanate groups comprises aromatic isocyanate groups which are especially derived from diphenylmethane 4,4'- or 2,4'- or 2,2'-diisocyanate or any desired mixtures of these isomers (MDI) or from tolylene 2,4- or 2,6-diisocyanate or any desired mixtures of these isomers (TDI).

Compositions having aromatic isocyanate groups are particularly inexpensive, cure rapidly and enable high stabilities. However, the storage stability, open time and faultless curing of such compositions are much more critical since aromatic isocyanate groups are much more reactive than aliphatic isocyanate groups.

Compositions based on MDI are particularly suitable as adhesive. They are particularly inexpensive and particularly reactive and enable particularly high strengths and durabilities. However, they are also particularly demanding in relation to storage stability, open time and blistering. Surprisingly, very good storage stabilities are obtained with the polyaldimine of the formula (I), coupled with a long open time and nevertheless reliably suppressed blistering. Similar polyaldimines which do not conform to the formula (I) typically result in MDI-based one-component compositions having limited storage stability and usually short open time.

Compositions based on TDI are particularly inexpensive and of particularly low viscosity. They enable low moduli of elasticity and hence particularly elastomeric properties. They are particularly suitable for applications in which movements are to be suppressed with low transmission of force, for example sealants for dilatation joins or coatings with markedly crack-bridging properties. However, they are also particularly demanding in relation to completeness of curing and plasticizer migration, especially with the modulus of elasticity set at a low level, which can be manifested in elevated surface tack. Surprisingly, with the polyaldimine of the formula (I), particularly low moduli of elasticity coupled with very low surface tack are obtained, whereas typically distinctly higher moduli of elasticity are obtained with similar polyaldimines which do not conform to the formula (I).

Particular preference is given to the use of at least one polyaldimine of the formula (I) as latent hardener for compositions containing isocyanate groups, where some or all of the isocyanate groups have been derived from diphenylmethane 4,4'- or 2,4'- or 2,2'-diisocyanate or any desired mixtures of these isomers (MDI). These compositions enable particularly high strengths and durabilities, but are also particularly demanding in relation to storage stability owing to the very high reactivity of MDI. Surprisingly, however, the polyaldimines of the formula (I) in compositions containing isocyanate groups based on MDI exhibit very good storage stability, whereas similar polyaldimines based on amines that do not conform to the formula (III), for example hexamethylenediamine, 1,3-bis(aminomethyl)cyclohexane (BAC) or 1,3-bis(aminomethyl)benzene (MXDA) are not storage-stable together with MDI and adducts thereof.

The invention further provides a composition comprising
at least one polyaldimine of the formula (I) and
at least one polyisocyanate and/or at least one polyurethane polymer containing isocyanate groups.

Suitable polyaldimines of the formula (I) are those described above.

A suitable polyisocyanate is especially a commercially available polyisocyanate, especially
  aromatic di- or triisocyanates, preferably diphenylmethane 4,4'- or 2,4'- or 2,2'-diisocyanate or any mixtures of these isomers (MDI), tolylene 2,4- or 2,6-diisocyanate or any mixtures of these isomers (TDI), mixtures of MDI and MDI homologs (polymeric MDI or PMDI), phenylene 1,3- or 1,4-diisocyanate, 2,3,5,6-tetramethyl-1,4-diisocyanatobenzene, naphthalene 1,5-diisocyanate (NDI), 3,3'-dimethyl-4,4'-diisocyanatodiphenyl (TODI), dianisidine diisocyanate (DADI), tris(4-isocyanatophenyl)methane or tris(4-isocyanatophenyl) thiophosphate; preferably MDI or TDI;
  aliphatic, cycloaliphatic or arylaliphatic di- or triisocyanates, preferably tetramethylene 1,4-diisocyanate, 2-methylpentamethylene 1,5-diisocyanate, hexamethylene 1,6-diisocyanate (HDI), 2,2,4- and/or 2,4,4-trimethylhexamethylene 1,6-diisocyanate (TMDI), decamethylene 1,10-diisocyanate, dodecamethylene 1,12-diisocyanate, lysine diisocyanate or lysine ester diisocyanate, cyclohexane 1,3- or 1,4-diisocyanate, 1-methyl-2,4- and/or -2,6-diisocyanatocyclohexane ($H_6$TDI), 1-isocyanato-3,3,5-trimethyl-5-isocyanatomethylcyclohexane (IPDI), perhydro-2,4'- and/or -4,4'-diphenylmethane diisocyanate ($H_{12}$MDI), 1,3- or 1,4-bis-(isocyanatomethyl)cyclohexane, m- or p-xylylene diisocyanate, tetramethylxylylene 1,3- or 1,4-diisocyanate, 1,3,5-tris(isocyanatomethyl)benzene, bis(1-isocyanato-1-methylethyl)naphthalene, dimer or trimer fatty acid isocyanates such as, in particular, 3,6-bis(9-isocyanatononyl)-4,5-di-(1-heptenyl)cyclohexene (dimeryl diisocyanate); preferably $H_{12}$MDI or HDI or IPDI;
  oligomers or derivatives of the di- or triisocyanates mentioned, especially derived from HDI, IPDI, MDI or TDI, especially oligomers containing uretdione or isocyanurate or iminooxadiazinedione groups or various groups among these; or di- or polyfunctional derivatives containing ester or urea or urethane or biuret or allophanate or carbodiimide or uretonimine or oxadiazinetrione groups or various groups among these. In practice, polyisocyanates of this kind are typically mixtures of substances having different degrees of oligomerization and/or chemical structures. They especially have an average NCO functionality of 2.1 to 4.0.

A particularly preferred polyisocyanate is HDI, IPDI, $H_{12}$MDI, TDI, MDI or a form of MDI which is liquid at room temperature.

A form of MDI which is liquid at room temperature is either 4,4'-MDI liquefied by partial chemical modification—especially carbodiimidization or uretonimine formation or adduct formation with polyols—or it is a mixture of 4,4'-MDI with other MDI isomers (2,4'-MDI and/or 2,2'-MDI), and/or with MDI oligomers and/or MDI homologs (PMDI), that has been brought about selectively by blending or results from the production process.

Most preferred is MDI or a room temperature liquid form of MDI.

A suitable polyurethane polymer containing isocyanate groups is especially obtained from the reaction of at least one polyol with a superstoichiometric amount of at least one polyisocyanate. The reaction is preferably conducted with exclusion of moisture at a temperature in the range from 50 to 160° C., optionally in the presence of suitable catalysts. The NCO/OH ratio is preferably in the range from 1.3/1 to 2.5/1. The polyisocyanate remaining after the conversion of the OH groups in the reaction mixture, especially monomeric diisocyanate, can be removed, especially by means of distillation, which is preferable in the case of a high NCO/OH ratio. The polyurethane polymer obtained preferably has a content of free isocyanate groups in the range from 0.5% to 10% by weight, especially 1% to 5% by weight, more preferably 1% to 3% by weight. The polyurethane polymer can optionally be prepared with additional use of plasticizers or solvents, in which case the plasticizers or solvents used do not contain any groups reactive toward isocyanates.

Preferred polyisocyanates for preparation of a polyurethane polymer containing isocyanate groups are the polyisocyanates already mentioned, especially the diisocyanates, especially MDI, TDI, IPDI, HDI or $H_{12}$MDI. Most preferred is MDI. This gives particularly high strengths and durabilities.

Suitable polyols are commercial polyols or mixtures thereof, especially
  polyether polyols, especially polyoxyalkylenediole and/or polyoxyalkylenetriols, especially polymerization products of ethylene oxide or 1,2-propylene oxide or 1,2- or 2,3-butylene oxide or oxetane or tetrahydrofuran or mixtures thereof, where these may have been polymerized with the aid of a starter molecule having two or more active hydrogen atoms, especially a starter molecule such as water, ammonia or a compound having multiple OH or NH groups, for example 1,2-ethanediol, 1,2- or 1,3-propanediol, neopentyl glycol, diethylene glycol, triethylene glycol, the isomeric dipropylene glycols or tripropylene glycols, the isomeric butanediols, pentanediols, hexanediols, heptanediols, octanediols, nonanediols, decanediols, undecanediols, 1,3- or 1,4-cyclohexanedimethanol, bisphenol A, hydrogenated bisphenol A, 1,1,1-trimethylolethane, 1,1,1-trimethylolpropane, glycerol or aniline, or mixtures of the aforementioned compounds. Likewise suitable are polyether polyols with polymer particles dispersed therein, especially those with styrene-acrylonitrile particles (SAN) or polyurea or polyhydrazodicarbonamide particles (PHD).

Preferred polyether polyols are polyoxypropylenediols or polyoxypropylenetriols, or what are called ethylene oxide-terminated (EO-endcapped) polyoxypropylenediols or -triols. The latter are mixed polyoxyethylene-polyoxypropylene polyols which are especially obtained in that polyoxypropylenediols or -triols, on conclusion of the polypropoxylation reaction, are further alkoxylated with ethylene oxide and hence ultimately have primary hydroxyl groups.

Preferred polyether polyols have a degree of unsaturation of less than 0.02 meq/g, especially less than 0.01 meq/g.

Polyester polyols, also called oligoesterols, prepared by known processes, especially the polycondensation of hydroxycarboxylic acids or lactones or the polycondensation of aliphatic and/or aromatic polycarboxylic acids with di- or polyhydric alcohols. Preference is given to polyester diols from the reaction of dihydric alcohols, such as, in particular, 1,2-ethanediol, diethylene glycol, 1,2-propanediol, dipropylene glycol, 1,4-butanediol, 1,5-pentanediol, 1,6-hexanediol, neopentyl glycol, glycerol, 1,1,1-trimethylolpropane or mixtures of the aforementioned alcohols, with organic dicarboxylic acids or the anhydrides or esters thereof, such as, in particular, succinic acid, glutaric acid, adipic acid, suberic acid, sebacic acid, dodecanedicarboxylic acid, maleic acid, fumaric acid, phthalic acid, isophthalic acid, terephthalic acid or hexahydrophthalic acid or mixtures of the aforementioned acids, or polyester polyols formed from lactones such as, in particular, ε-caprolactone. Particular preference is given to polyester polyols formed from adipic acid or sebacic acid or dodecanedicarboxylic acid and hexanediol or neopentyl glycol.

Polycarbonate polyols as obtainable by reaction, for example, of the abovementioned alcohols—used to form the polyester polyols—with dialkyl carbonates, diaryl carbonates or phosgene.

Block copolymers bearing at least two hydroxyl groups and having at least two different blocks having polyether, polyester and/or polycarbonate structure of the type described above, especially polyether polyester polyols.

Polyacrylate polyols and polymethacrylate polyols.

Polyhydroxy-functional fats and oils, for example natural fats and oils, especially castor oil; or polyols obtained by chemical modification of natural fats and oils—called oleochemical polyols—for example the epoxy polyesters or epoxy polyethers obtained by oxidation of unsaturated oils and subsequent ring opening with carboxylic acids or alcohols, or polyols obtained by hydroformylation and hydrogenation of unsaturated oils; or polyols obtained from natural fats and oils by degradation processes such as alcoholysis or ozonolysis and subsequent chemical linkage, for example by transesterification or dimerization, of the degradation products or derivatives thereof thus obtained. Suitable degradation products of natural fats and oils are especially fatty acids and fatty alcohols, and also fatty acid esters, especially the methyl esters (FAME), which can, for example, be derivatized to hydroxy fatty acid esters by hydroformylation and hydrogenation.

Polyhydrocarbon polyols, also called oligohydrocarbonols, for example polyhydroxy-functional polyolefins, polyisobutylenes, polyisoprenes; polyhydroxy-functional ethylene-propylene, ethylene-butylene or ethylene-propylene-diene copolymers as produced, for example, by Kraton Polymers; polyhydroxy-functional polymers of dienes, especially of 1,3-butadiene, which can especially also be prepared from anionic polymerization; polyhydroxy-functional copolymers of dienes such as 1,3-butadiene or diene mixtures and vinyl monomers such as styrene, acrylonitrile, vinyl chloride, vinyl acetate, vinyl alcohol, isobutylene and isoprene, for example polyhydroxy-functional acrylonitrile/butadiene copolymers as preparable, for example, from epoxides or amino alcohols and carboxyl-terminated acrylonitrile/butadiene copolymers (commercially available, for example, under the Hypro® CTBN or CTBNX or ETBN name from Emerald Performance Materials); and hydrogenated polyhydroxy-functional polymers or copolymers of dienes.

Also especially suitable are mixtures of polyols.

Preference is given to polyether polyols, polyester polyols, polycarbonate polyols, poly(meth)acrylate polyols or polybutadiene polyols.

Particular preference is given to polyether polyols, polyester polyols, especially aliphatic polyester polyols, or polycarbonate polyols, especially aliphatic polycarbonate polyols.

Most preferred are polyether polyols, especially polyoxypropylenedi- or triols or ethylene oxide-terminated polyoxypropylenedi- or triols.

Preference is given to polyols having an average molecular weight in the range from 400 to 20,000 g/mol, preferably from 1,000 to 15,000 g/mol.

Preference is given to polyols having an average OH functionality in the range from 1.6 to 3.

Preference is given to polyols that are liquid at room temperature.

In the preparation of a polyurethane polymer containing isocyanate groups, it is also possible to use fractions of di- or polyfunctional alcohols, especially 1,2-ethanediol, 1,2-propanediol, 1,3-propanediol, 2-methyl-1,3-propanediol, 1,2-butanediol, 1,3-butanediol, 1,4-butanediol, 1,3-pentanediol, 1,5-pentanediol, 3-methyl-1,5-pentanediol, neopentyl glycol, dibromoneopentyl glycol, 1,2-hexanediol, 1,6-hexanediol, 1,7-heptanediol, 1,2-octanediol, 1,8-octanediol, 2-ethyl-1,3-hexanediol, diethylene glycol, triethylene glycol, dipropylene glycol, tripropylene glycol, 1,3- or 1,4-cyclohexanedimethanol, ethoxylated bisphenol A, propoxylated bisphenol A, cyclohexanediol, hydrogenated bisphenol A, dimer fatty acid alcohols, 1,1,1-trimethylolethane, 1,1,1-trimethylolpropane, glycerol, pentaerythritol, sugar alcohols such as, in particular, xylitol, sorbitol and mannitol, or sugars such as, in particular, sucrose, or alkoxylated derivatives of the alcohols mentioned or mixtures of the alcohols mentioned.

The polyurethane polymer containing isocyanate groups preferably has an average molecular weight in the range from 1,500 to 20,000 g/mol, especially 2,000 to 15,000 g/mol.

It is preferably liquid at room temperature.

The composition preferably comprises at least one polyurethane polymer containing isocyanate groups.

Preferably, the polyurethane polymer containing isocyanate groups has aromatic isocyanate groups which are especially derived from diphenylmethane 4,4'- or 2,4'- or 2,2'-diisocyanate or any desired mixtures of these isomers (MDI) or from tolylene 2,4- or 2,6-diisocyanate or any desired mixtures of these isomers (TDI).

Most preferably, the composition comprises a polyurethane polymer containing isocyanate groups, the isocyanate groups of which are derived partly or wholly from diphenylmethane 4,4'- or 2,4'- or 2,2'-diisocyanate or any desired mixtures of these isomers (MDI). This achieves particularly high strengths and durabilities.

In addition to a polyurethane polymer containing isocyanate groups, the composition may further comprise at least one diisocyanate and/or an oligomer or polymer of a diisocyanate, especially a room temperature liquid form of MDI or PMDI or an IPDI isocyanurate or TDI oligomer or a mixed isocyanurate based on TDI/HDI or an HDI oligomer.

Preferably, the composition comprises, as well as at least one polyaldimine of the formula (I) and at least one polyisocyanate, additionally one or more further constituents which are especially selected from catalysts, fillers, plasticizers and solvents.

Suitable catalysts are especially catalysts for the hydrolysis of the aldimino groups, especially organic acids, especially carboxylic acids such as 2-ethylhexanoic acid, lauric acid, stearic acid, isostearic acid, oleic acid, neodecanoic acid, benzoic acid, salicylic acid or 2-nitrobenzoic acid, organic carboxylic anhydrides such as phthalic anhydride, hexahydrophthalic anhydride or methylhexahydrophthalic anhydride, silyl esters of carboxylic acids, organic sulfonic acids such as methanesulfonic acid, p-toluenesulfonic acid or 4-dodecylbenzenesulfonic acid, sulfonic esters, other organic or inorganic acids, or mixtures of the aforementioned acids and acid esters. Particular preference is given to carboxylic acids, especially aromatic carboxylic acids such as benzoic acid, 2-nitrobenzoic acid or especially salicylic acid.

Suitable catalysts are additionally catalysts for the acceleration of the reaction of isocyanate groups, especially organotin(IV) compounds such as, in particular, dibutyltin diacetate, dibutyltin dilaurate, dibutyltin dichloride, dibutyltin diacetylacetonate, dimethyltin dilaurate, dioctyltin diacetate, dioctyltin dilaurate or dioctyltin diacetylacetonate, complexes of bismuth(III) or zirconium(IV), especially with ligands selected from alkoxides, carboxylates, 1,3-diketonates, oxinate, 1,3-ketoesterates and 1,3-ketoamidates, or compounds containing tertiary amino groups, such as, in particular, 2,2'-dimorpholinodiethyl ether (DMDEE).

Also especially suitable are combinations of different catalysts.

Suitable fillers are especially ground or precipitated calcium carbonates, optionally coated with fatty acids, especially stearates, or barytes, quartz flours, quartz sands, dolomites, wollastonites, kaolins, calcined kaolins, sheet silicates such as mica or talc, zeolites, aluminum hydroxides, magnesium hydroxides, silicas including finely divided silicas from pyrolysis processes, cements, gypsums, fly ashes, industrially produced carbon blacks, graphite, metal powders, for example of aluminum, copper, iron, silver or steel, PVC powders or hollow beads.

Suitable plasticizers are especially carboxylic esters such as phthalates, especially diisononyl phthalate (DINP), diisodecyl phthalate (DIDP) or di(2-propylheptyl) phthalate (DPHP), hydrogenated phthalates, especially hydrogenated diisononyl phthalate (DINCH), terephthalates, especially dioctyl terephthalate, trimellitates, adipates, especially dioctyl adipate, azelates, sebacates, benzoates, glycol ethers, glycol esters, organic phosphoric or sulfonic esters, polybutenes, polyisobutenes, or plasticizers derived from natural fats or oils, especially epoxidized soybean oil or linseed oil.

Suitable solvents are especially acetone, methyl ethyl ketone, methyl n-propyl ketone, diisobutyl ketone, methyl isobutyl ketone, methyl n-amyl ketone, methyl isoamyl ketone, acetylacetone, mesityl oxide, cyclohexanone, methylcyclohexanone, ethyl acetate, propyl acetate, butyl acetate, n-butyl propionate, diethyl malonate, 1-methoxy-2-propyl acetate, ethyl 3-ethoxypropionate, diisopropyl ether, diethyl ether, dibutyl ether, diethylene glycol diethyl ether, ethylene glycol diethyl ether, ethylene glycol monopropyl ether, ethylene glycol mono-2-ethylhexyl ether, toluene, xylene, heptane, octane, naphtha, white spirit, petroleum ether or benzine, especially Solvesso™ products (from Exxon), and also methylene chloride, propylene carbonate, butyrolactone, N-methylpyrrolidone or N-ethylpyrrolidone.

The composition may comprise further additives commonly used for polyurethane compositions. More particularly, the following auxiliaries and additives may be present:

- inorganic or organic pigments, especially titanium dioxide, chromium oxides or iron oxides;
- fibers, especially glass fibers, carbon fibers, metal fibers, ceramic fibers, polymer fibers such as polyamide fibers or polyethylene fibers, or natural fibers such as wool, cellulose, hemp or sisal;
- dyes;
- desiccants, especially molecular sieve powder, calcium oxide, highly reactive isocyanates such as p-tosyl isocyanate, monomeric diisocyanates, monooxazolidines such as Incozol® 2 (from Incorez) or orthoformic esters;
- adhesion promoters, especially organoalkoxysilanes, especially epoxysilanes such as, in particular, 3-glycidoxypropyltrimethoxysilane or 3-glycidoxypropyltriethoxysilane, (meth)acrylosilanes, anhydridosilanes, carbamatosilanes, alkylsilanes or iminosilanes, or oligomeric forms of these silanes, or titanates;
- latent hardeners or crosslinkers, especially ketimines, enamines, oxazolidines or aldimines not conforming to the formula (I);
- further catalysts which accelerate the reaction of the isocyanate groups, especially salts, soaps or complexes of tin, zinc, bismuth, iron, aluminum, molybdenum, dioxomolybdenum, titanium, zirconium or potassium, especially tin(II) 2-ethylhexanoate, tin(II) neodecanoate, zinc(II) acetate, zinc(II) 2-ethylhexanoate, zinc(II) laurate, zinc(II) acetylacetonate, aluminum lactate, aluminum oleate, diisopropoxytitanium bis(ethylacetoacetate) or potassium acetate; compounds containing tertiary amino groups, especially N-ethyldiisopropylamine, N,N,N',N'-tetramethylalkylenediamines, pentamethylalkylenetriamines and higher homologs thereof, bis(N,N-diethylaminoethyl) adipate, tris(3-dimethylaminopropyl)amine, 1,4-diazabicyclo[2.2.2]octane (DABCO), 1,8-diazabicyclo [5.4.0]undec-7-ene (DBU), 1,5-diazabicyclo[4.3.0] non-5-ene (DBN), N-alkylmorpholines, N,N'-dimethylpiperazine; aromatic nitrogen compounds such as 4-dimethylam inopyridine, N-methylimidazole, N-vinylimidazole or 1,2-dimethylimidazole; organic ammonium compounds such as benzyltrimethylammonium hydroxide or alkoxylated tertiary amines; what are called "delayed action" catalysts, which are modifications of known metal or amine catalysts;
- rheology modifiers, especially thickeners, especially sheet silicates such as bentonites, derivatives of castor oil, hydrogenated castor oil, polyam ides, polyamide waxes, polyurethanes, urea compounds, fumed silicas, cellulose ethers or hydrophobically modified polyoxyethylenes;

natural resins, fats or oils such as rosin, shellac, linseed oil, castor oil or soya oil;

nonreactive polymers, especially homo- or copolymers of unsaturated monomers, especially from the group comprising ethylene, propylene, butylene, isobutylene, isoprene, vinyl acetate or alkyl (meth)acrylates, especially polyethylenes (PE), polypropylenes (PP), polyisobutylenes, ethylene-vinyl acetate copolymers (EVA) or atactic poly-α-olefins (APAO);

flame-retardant substances, especially the aluminum hydroxide or magnesium hydroxide fillers already mentioned, and also, in particular, organic phosphoric esters such as, in particular, triethyl phosphate, tricresyl phosphate, triphenyl phosphate, diphenyl cresyl phosphate, isodecyl diphenyl phosphate, tris(1,3-dichloro-2-propyl) phosphate, tris(2-chloroethyl) phosphate, tris(2-ethylhexyl) phosphate, tris(chloroisopropyl) phosphate, tris(chloropropyl) phosphate, isopropylated triphenyl phosphate, mono-, bis- or tris(isopropylphenyl) phosphates of different degrees of isopropylation, resorcinol bis(diphenyl phosphate), bisphenol A bis (diphenyl phosphate) or ammonium polyphosphates;

additives, especially wetting agents, leveling agents, defoamers, deaerators, stabilizers against oxidation, heat, light or UV radiation, or biocides;

or further substances customarily used in moisture-curing compositions.

It may be advisable to chemically or physically dry certain substances before mixing them into the composition.

More particularly, the composition may, as well as the polyamine of formula (I), comprise further latent hardeners, especially polyaldimines which do not conform to the formula (I), or oxazolidines.

In the composition, the ratio between aldimino groups and isocyanate groups is preferably in the range from 0.05 to 1.1, more preferably in the range from 0.1 to 1.0, especially in the range from 0.2 to 0.9.

The composition preferably contains a content of polyisocyanates and of polyurethane polymers containing isocyanate groups in the range from 5% to 90% by weight, especially 10% to 80% by weight.

The composition is especially produced with exclusion of moisture and stored at ambient temperature in moisture-tight containers. A suitable moisture-tight container especially consists of an optionally coated metal and/or plastic, and is especially a vat, a container, a hobbock, a bucket, a canister, a can, a bag, a tubular bag, a cartridge or a tube.

The composition may take the form of a one-component or of a multi-component, especially two-component, composition.

A composition referred to as a "one-component" composition is one in which all constituents of the composition are in the same container and which is storage-stable per se.

A composition referred to as a "two-component" composition is one in which the constituents of the composition are in two different components which are stored in separate containers and are not mixed with one another until shortly before or during the application of the composition.

The composition is preferably a one-component composition. Given suitable packaging and storage, it is storage-stable, typically over several months up to one year or longer.

On application of the composition, the process of curing commences. This results in the cured composition.

In the case of a one-component composition, it is applied as such and then begins to cure under the influence of moisture or water. For acceleration of the curing, an accelerator component which contains or releases water and/or a catalyst can be mixed into the composition on application, or the composition can be contacted with such an accelerator component after application thereof. In the case of a two-component composition, it is applied after the mixing of the two components and begins to cure by internal reaction, and the curing may be completed by the action of external moisture. The two components can be mixed continuously or batchwise with dynamic mixers or static mixers.

In the curing, the isocyanate groups react under the influence of moisture with the aldimino groups of the polyaldimine of the formula (I) and any further blocked amino groups present. Some of the isocyanate groups, especially the excess isocyanate groups relative to the aldimino groups, react with one another under the influence of moisture and/or with any further reactive groups present in the composition, especially hydroxyl groups or free amino groups. The totality of these reactions of isocyanate groups that lead to curing of the composition is also referred to as crosslinking.

The moisture required for curing of the one-component composition preferably gets into the composition through diffusion from the air (air humidity). This forms a solid layer of cured composition ("skin") on the surfaces of the composition that are in contact with air. The curing continues in the direction of diffusion from the outside inward, the skin becoming increasingly thick and ultimately encompassing the entire composition applied. The moisture can also get into the composition additionally or entirely from one or more substrate(s) to which the composition has been applied and/or can come from an accelerator component which is mixed into the composition on application or is contacted therewith after application, for example by painting or spraying. Any external humidity required to complete the curing of a two-component composition preferably comes from the air and/or from the substrates.

The composition is preferably applied at ambient temperature, especially in the range from about 0 to 50° C., preferably in the range from 5 to 40° C.

The composition is preferably likewise cured at ambient temperature.

The composition has a comparatively long open time.

The "open time" refers to the period of time over which the composition can be worked or reworked after the curing process has commenced.

The time until formation of a skin ("skin time") or until freedom from tack ("tack-free time") is a measure of the open time.

The crosslinking releases an aldehyde of the formula (IV). It is substantially nonvolatile and odorless and remains for the most part in the cured composition. It behaves or acts like a plasticizer therein. As such, it can in principle itself migrate and/or affect the migration of plasticizers. The aldehyde of the formula (IV) has very good compatibility with the cured composition, barely migrates itself, and also does not trigger any enhanced migration of plasticizers.

The composition is preferably an adhesive or a sealant or a coating.

The adhesive or sealant or coating is preferably elastic.

The composition is especially suitable as an adhesive and/or sealant for bonding and sealing applications, especially in the construction and manufacturing industries or in motor-vehicle construction, especially for parquet bonding, installable component bonding, cavity sealing, assembly, module bonding, chassis bonding, glass bonding, join sealing or anchoring. Elastic bonds in motor vehicle construction are especially the attachment of parts such as plastic covers, decorative strips, flanges, fenders, drivers' cabins or other installable components to the painted chassis of a motor vehicle, or the bonding of glass panes into the chassis, where the motor vehicles are especially automobiles, trucks, buses, rail vehicles or ships.

The composition is especially suitable as a sealant for the elastic sealing of all kinds of joins, seams or cavities especially of joins in construction such as dilatation joins or connection joins between components. A sealant having elastomeric properties is particularly suitable especially for the sealing of dilatation joins in built structures.

As a coating, the composition is suitable for protection of floors or walls, especially as coating of balconies, terraces, open spaces, bridges, parking decks, or for sealing of roofs, especially flat roofs or slightly inclined roof areas or roof gardens, or in the interior of buildings for water sealing, for example beneath tiles or ceramic plates in wet cells or kitchens, or as floorcovering in kitchens, industrial halls or fabrication spaces, or as seal in collection tanks, channels, shafts or wastewater treatment plants, or protection of surfaces as varnish or seal, or as potting compound for cavity sealing, as seam seal or as protective coating for pipes, for example.

It can also be used for repair purposes as seal or coating, for example of leaking roof membranes or floor coverings that are no longer fit for purpose, or more particularly as repair compound for highly reactive spray seals.

The composition can be formulated such that it has a pasty consistency with structurally viscous properties. A composition of this kind is applied by means of a suitable device, for example from standard commercial cartridges or vats or hobbocks, for example in the form of a bead, which may have an essentially round or triangular cross-sectional area.

The composition can also be formulated such that it is fluid and "self-leveling" or only slightly thixotropic and can be poured out for application. As a coating, it can subsequently be distributed, for example, over an area down to the desired layer thickness, for example by means of a roller, a slide bar, a notched trowel or a palette knife. In one operation, typically a layer thickness in the range from 0.5 to 3 mm, especially 1.0 to 2.5 mm, is applied.

Suitable substrates which can be bonded or sealed or coated with the composition are especially
- glass, glass ceramic, concrete, mortar, fiber cement, especially fiber cement boards, brick, tile, gypsum, especially gypsum boards, or natural stone such as granite or marble;
- repair or leveling compounds based on PCC (polymer-modified cement mortar) or ECC (epoxy resin-modified cement mortar);
- metals or alloys, such as aluminum, copper, iron, steel, nonferrous metals, including surface-finished metals, or alloys such as galvanized or chromed metals;
- asphalt or bitumen;
- leather, textiles, paper, wood, woodbase materials bonded with resins such as phenolic, melamine or epoxy resins, resin-textile composites or further polymer composites;
- plastics such as rigid and flexible PVC, polycarbonate, polystyrene, polyester, polyamide, PMMA, ABS, SAN, epoxy resins, phenolic resins, PUR, POM, TPO, PE, PP, EPM or EPDM, in each case untreated or surface-treated, for example by means of plasma, corona or flames;
- fiber-reinforced plastics, such as carbon fiber-reinforced plastics (CFP), glass fiber-reinforced plastics (GFP) and sheet molding compounds (SMC);
- insulation foams, especially made of EPS, XPS, PUR, PIR, rockwool, glass wool or foamed glass;
- coated or painted substrates, especially painted tiles, coated concrete, powder-coated metals or alloys or painted metal sheets;
- paints or varnishes, especially automotive topcoats.

If required, the substrates can be pretreated prior to application, especially by physical and/or chemical cleaning methods or the application of an activator or a primer.

It is possible to bond and/or seal two identical or two different substrates.

The application and curing of the composition affords an article bonded or sealed or coated with the composition. This article may be a built structure or a part thereof, especially a built structure in civil engineering above or below ground, a bridge, a roof, a staircase or a facade, or it may be an industrial good or a consumer good, especially a window, a pipe, a rotor blade of a wind turbine, a domestic appliance or a mode of transport such as, in particular, an automobile, a bus, a truck, a rail vehicle, a ship, an aircraft or a helicopter, or an installable component thereof.

The composition of the invention has advantageous properties. It is particularly storage-stable with exclusion of moisture, even in the case of highly reactive aromatic isocyanate groups such as those of MDI. It has a comparatively long open time which enables seamless leveling of the material applied or positioning or readjustment of the objects bonded therewith over a prolonged period after application, which is important, for example, in the case of coatings over a large area or long sealing strips, or in the case of bonding of large or complex objects. The curing proceeds rapidly, in a blister-free manner and without troublesome odor immissions, giving rise to a cured material having good strength, extensibility and elasticity which does not tend to have problems with plasticizer migration such as bleeding, substrate discoloration or stress-cracking in the substrate.

EXAMPLES

Adduced hereinafter are working examples which are intended to elucidate the invention described in detail. It will be appreciated that the invention is not restricted to these described working examples.

Aldehydes Used:
Aldehyde—1: Fractionated reaction mixture obtained from formylation, catalyzed by means of HF—$BF_3$, of $C_{10-14}$-alkylbenzene, containing mainly branched 4-($C_{10-14}$-alkyl)benzaldehydes. (mean aldehyde equivalent weight 290 g/eq)
p-Decyloxybenzaldehyde (262.4 g/mol)
2,2-Dimethyl-3-lauroyloxypropanal (284.4 g/mol)
Benzaldehyde (106.1 g/mol)
p-tert-Butylbenzaldehyde (162.2 g/mol)
3-Phenoxybenzaldehyde (198.2 g/mol)
Aldehyde-1 is a mixture of aldehydes of the formula (IV) and p-decyloxybenzaldehyde is an aldehyde of the formula (IV), whereas 2,2-dimethyl-3-lauroyloxypropanal, benzaldehyde, p-tert-butylbenzaldehyde and 3-phenoxybenzaldehyde do not conform to the formula (IV).

Amines and Abbreviations Used:
IPDA  3-aminomethyl-3,5,5-trimethylcyclohexylamine (Vestamin® IPD from Evonik, 170.3 g/mol)
NBDA  2,5(6)-bis(aminomethyl)bicyclo[2.2.1]heptane (PRO-NBDA from Mitsui Fine Chemicals, 154.3 g/mol)

TCD 3(4),8(9)-di(aminomethyl)tricyclo[5.2.1.0(2.6)]decane (TCD diamine from Oxea, 194.3 g/mol)
TMD 2,2,4- and 2,4,4-trimethylhexamethylenediamine (Vestamin® TMD from Evonik, 158.4 g/mol)
MPMD 1,5-diamino-2-methylpentane (Dytek® A from Invista, 116 g/mol)
1,2-PDA 1,2-propylenediamine (from BASF, 74.1 g/mol)
$H_{12}$MDA 4,4'-diaminodicyclohexylmethane (from BASF, 210.4 g/mol)
T-403 polyoxypropylenetriamine having an average molecular weight of about 440 g/mol (Jeffamine® T-403, from Huntsman, amine value 359 mg KOH/g)
HDA hexane-1,6-diamine (from Invista, 116.2 g/mol)
MXDA 1,3-bis(aminomethyl)benzene (from Mitsubishi Gas Chem., 136.2 g/mol)
pPhDA 1,4-phenylenediamine (from Sigma-Aldrich, 108.2 g/mol)

Preparation of Polyaldimines:

The amine value (including aldimino groups) was determined by means of titration (with 0.1 N $HClO_4$ in acetic acid versus crystal violet).

The viscosity was measured with a thermostated Rheotec RC30 cone-plate viscometer (cone diameter 50 mm, cone angle 1°, cone tip-plate distance 0.05 mm, shear rate 10 $s^{-1}$).

Aldimine A1:
50.00 g of aldehyde-1 were initially charged in a round-bottom flask under a nitrogen atmosphere. While stirring, 13.93 g of IPDA were added and then the volatile constituents were removed at 80° C. and a reduced pressure of 10 mbar. A light yellow, odorless and pH-neutral liquid having a viscosity at 20° C. of 21.3 Pa·s and an amine value of 150.1 mg KOH/g was obtained.

Aldimine A2:
50.00 g of aldehyde-1 were initially charged in a round-bottom flask under a nitrogen atmosphere. While stirring, 12.62 g of NBDA were added and then the volatile constituents were removed at 80° C. and a reduced pressure of 10 mbar. A light yellow, odorless and pH-neutral liquid having a viscosity at 20° C. of 9.8 Pa·s and an amine value of 152.3 mg KOH/g was obtained.

Aldimine A3:
50.00 g of aldehyde-1 were initially charged in a round-bottom flask under a nitrogen atmosphere. While stirring, 15.90 g of TCD were added and then the volatile constituents were removed at 80° C. and a reduced pressure of 10 mbar. A light yellow, odorless and pH-neutral liquid having a viscosity at 20° C. of 19.6 Pa·s and an amine value of 144.0 mg KOH/g was obtained.

Aldimine A4:
50.00 g of aldehyde-1 were initially charged in a round-bottom flask under a nitrogen atmosphere. While stirring, 17.21 g of $H_{12}$MDA were added and then the volatile constituents were removed at 80° C. and a reduced pressure of 10 mbar. A light yellow, odorless and pH-neutral liquid having a viscosity at 20° C. of 59.6 Pa·s and an amine value of 140.2 mg KOH/g was obtained.

Aldimine A5:
50.00 g of aldehyde-1 were initially charged in a round-bottom flask under a nitrogen atmosphere. While stirring, 12.95 g of TMD were added and then the volatile constituents were removed at 80° C. and a reduced pressure of 10 mbar. A light yellow, odorless and pH-neutral liquid having a viscosity at 20° C. of 1.6 Pa·s and an amine value of 152.4 mg KOH/g was obtained.

Aldimine A6:
50.00 g of aldehyde-1 were initially charged in a round-bottom flask under a nitrogen atmosphere. While stirring, 9.51 g of MPMD were added and then the volatile constituents were removed at 80° C. and a reduced pressure of 10 mbar. A light yellow, odorless and pH-neutral liquid having a viscosity at 20° C. of 1.2 Pa·s and an amine value of 162.0 mg KOH/g was obtained.

Aldimine A7:
50.00 g of aldehyde-1 were initially charged in a round-bottom flask under a nitrogen atmosphere. While stirring, 25.77 g of T-403 were added and then the volatile constituents were removed at 80° C. and a reduced pressure of 10 mbar. An orange-yellow, odorless and pH-neutral liquid having a viscosity at 20° C. of 4.3 Pa·s and an amine value of 126.8 mg KOH/g was obtained.

Aldimine A8:
5.75 g of decyloxybenzaldehyde were initially charged in a round-bottom flask under a nitrogen atmosphere. While stirring, 1.78 g of IPDA were added and then the volatile constituents were removed at 80° C. and a reduced pressure of 10 mbar. A solid which was waxy at 20° C., odorless and pH-neutral with an amine value of 163.7 mg KOH/g and a melting point of 52 to 59° C. and a viscosity at 80° C. of 82.4 Pa·s was obtained.

Aldimine R1:
50.00 g of aldehyde-1 were initially charged in a round-bottom flask under a nitrogen atmosphere. While stirring, 13.58 g of HDA solution (70% by weight in water) were added and then the volatile constituents were removed at 80° C. and a reduced pressure of 10 mbar. A light yellow, odorless and pH-neutral liquid having a viscosity at 20° C. of 1.0 Pa·s and an amine value of 161.6 mg KOH/g was obtained.

Aldimine R2:
50.00 g of aldehyde-1 were initially charged in a round-bottom flask under a nitrogen atmosphere. While stirring, 11.14 g of MXDA were added and then the volatile constituents were removed at 80° C. and a reduced pressure of 10 mbar. A pale yellow, odorless and pH-neutral liquid having a viscosity at 20° C. of 2.6 Pa·s and an amine value of 155.7 mg KOH/g was obtained.

Aldimine R3:
50.00 g of aldehyde-1 were initially charged in a round-bottom flask under a nitrogen atmosphere. While stirring, 8.85 g of pPhDA were added and then the volatile constituents were removed at 80° C. and a reduced pressure of 10 mbar. An orange-brown, odorless and pH-neutral liquid having a viscosity at 20° C. of 4.9 Pa·s and an amine value of 163.0 mg KOH/g was obtained.

Aldimine R4:
48.92 of 2,2-dimethyl-3-lauroyloxypropanal were initially charged in a round-bottom flask under a nitrogen atmosphere. While stirring, 13.93 g of IPDA were added and then the volatile constituents were removed at 80° C. and a reduced pressure of 10 mbar. A pale yellow, odorless liquid having an amine value of 153.0 mg KOH/g was obtained.

Aldimine R5:
48.87 g of 2,2-dimethyl-3-lauroyloxypropanal were initially charged in a round-bottom flask under a nitrogen atmosphere. While stirring, 17.21 g of $H_{12}$MDA were added and then the volatile constituents were removed at 80° C. and a reduced pressure of 10 mbar. A light yellow, odorless liquid having a viscosity at 20° C. of 0.6 Pa·s and an amine value of 145.4 mg KOH/g was obtained.

Aldimine R6:
33.43 g of benzaldehyde were initially charged in a round-bottom flask under a nitrogen atmosphere. While stirring, 25.55 g of IPDA were added and then the volatile constituents were removed at 80° C. and a reduced pressure of 10 mbar. What was obtained was a light yellow, intensely odorous liquid having an amine value of 314.1 mg KOH/g, which crystallized after a few days.

Aldimine R7:

27.87 g of p-tert-butylbenzaldehyde were initially charged in a round-bottom flask under a nitrogen atmosphere. While stirring, 13.93 g of IPDA were added and then the volatile constituents were removed at 80° C. and a reduced pressure of 10 mbar. What was obtained was a light yellow, intensely odorous, highly viscous liquid having an amine value of 236.2 mg KOH/g, which crystallized after a few days. The viscosity at 80° C. was 23.7 Pa·s.

Aldimine R8:

34.06 g of 3-phenoxybenzaldehyde were initially charged in a round-bottom flask under a nitrogen atmosphere. While stirring, 13.93 g of IPDA were added and then the volatile constituents were removed at 80° C. and a reduced pressure of 10 mbar. What was obtained was a light yellow, highly viscous liquid with low odor and having an amine value of 203.8 mg KOH/g, which crystallized after a few days. The viscosity at 80° C. was 5.1 Pa·s.

The aldimines A1 to A8 are polyaldimines of the formula (I). The aldimines R1 to R8 are comparative examples.

Preparation of Polymers Containing Isocyanate Groups

Polymer P1:

4000 g of polyoxypropylenediol (Acclaim® 4200, from Covestro; OH number 28.5 mg KOH/g) and 520 g of diphenylmethane 4,4'-diisocyanate (Desmodur® 44 MC L, from Covestro) were reacted by a known method at 80° C. to give an NCO-terminated polyurethane polymer which is liquid at room temperature and has a content of free isocyanate groups of 1.85% by weight.

Polymer P2:

3080 g of polyoxypropylenediol (Acclaim® 4200, from Covestro; OH number 28.5 mg KOH/g), 1540 g of polyoxypropylenepolyoxyethylenetriol (Caradol® MD34-02, from Shell; OH number 35.0 mg KOH/g) and 385 g of tolylene diisocyanate (Desmodur® T 80 P, Covestro) were reacted at 80° C. by a known method to give an NCO-terminated polyurethane polymer which is liquid at room temperature and has a content of free isocyanate groups of 1.50% by weight.

Polymer P3:

590 g of polyoxypropylenediol (Acclaim® 4200, from Covestro; OH number 28.5 mg KOH/g), 1180 g of polyoxypropylenepolyoxyethylenetriol (Caradol® MD34-02, from Shell; OH number 35.0 mg KOH/g) and 230 g of isophorone diisocyanate (Vestanat® IPDI, Degussa) were reacted by a known method at 80° C. to give an NCO-terminated polyurethane polymer which is liquid at room temperature and has a content of free isocyanate groups of 2.10% by weight.

Polymer P4:

300.0 g of polyoxypropylenepolyoxyethylenediol (Desmophen® L300, from Covestro; OH number 190.0 mg KOH/g) and 228.8 g of isophorone diisocyanate (Vestanat® IPDI, Degussa) were reacted by a known method at 60° C. to give an NCO-terminated polyurethane polymer which is liquid at room temperature and has a content of free isocyanate groups of 8.35% by weight.

One-Component Compositions

Compositions Z1 to Z15 and Ref1 to Ref10

For each composition, the ingredients specified in tables 1 to 3 were mixed in the amounts specified (in parts by weight) by means of a centrifugal mixer (SpeedMixer™ DAC 150, FlackTek Inc.) with exclusion of moisture at 3000 rpm for one minute and stored with exclusion of moisture. Each composition was tested as follows:

As a measure of storage stability, the Viscosity (1 d RT) was determined the day after production, and the Viscosity (7 d 60° C.) after storage in a closed container in an air circulation oven at 60° C. for 7 days. The viscosity was measured, at a temperature of 20° C. in each case, with a thermostated Rheotec RC30 cone-plate viscometer (cone diameter 50 mm, cone angle 1°, cone tip-plate distance 0.05 mm, shear rate 10 s$^{-1}$). A significant rise in the viscosity on storage shows inadequate storage stability.

As a measure of the open time, the Tack-free time was determined. For this purpose, a few grams of the composition were applied to cardboard in a layer thickness of about 2 mm and, under standard climatic conditions, the time until, when the surface of the composition was gently tapped by means of an LDPE pipette, there were for the first time no residues remaining any longer on the pipette was determined.

To determine the mechanical properties, each composition was poured onto a PTFE-coated film to give a film of thickness 2 mm and stored under standard climatic conditions for 7 days, and a few dumbbells having a length of 75 mm with a bar length of 30 mm and a bar width of 4 mm were punched out of the film and these were tested in accordance with DIN EN 53504 at a strain rate of 200 mm/minute for Tensile strength (breaking force), Elongation at break, Modulus of elasticity 5% (at 0.5-5% elongation) and Modulus of elasticity 50% (at 0.5-50% elongation).

Appearance was assessed visually on the films produced. "Nice" was used to describe a clear film with a nontacky surface without blisters.

Odor was assessed by smelling by nose at a distance of 2 cm from the freshly produced films. "No" means that no odor was perceptible.

The results are reported in tables 1 to 3.

Compositions Z1 to Z15 are inventive examples. Compositions Ref1 to Ref10 are comparative examples.

TABLE 1

Composition (in parts by weight) and properties of Z1 to Z7 and Ref1 to Ref8.

| | Composition | | | | | | |
|---|---|---|---|---|---|---|---|
| | Z1 | Z2 | Z3 | Z4 | Z5 | Z6 | Z7 |
| Polymer P1 | 80.00 | 80.00 | 80.00 | 80.00 | 80.00 | 80.00 | 80.00 |
| Aldimine | A1 | A2 | A3 | A4 | A5 | A6 | A8 |
| | 9.20 | 8.98 | 9.48 | 9.67 | 9.03 | 8.52 | 8.44[2] |
| Salicylic acid solution[1] | 1.50 | 1.50 | 1.50 | 1.50 | 1.50 | 1.50 | 1.50 |
| Viscosity (1 d RT) | 29.4 | 43.1 | 47.8 | 32.0 | 43.4 | 41.7 | 34.8 |
| [Pa · s] (7 d 60° C.) | 34.8 | 65.3 | 69.5 | 37.5 | 50.3 | 57.9 | 42.3 |
| Tack-free time | 1 h 20' | 1 h | 1 h 13' | 1 h 10' | 1 h 40' | 1 h 5' | 2 h 10' |

TABLE 1-continued

Composition (in parts by weight) and properties of Z1 to Z7 and Ref1 to Ref8.

| | | | | | | | |
|---|---|---|---|---|---|---|---|
| Tensile strength [MPa] | 1.62 | 1.76 | 2.01 | 3.46 | 1.60 | 1.90 | 2.62 |
| Elongation at break [%] | 1240 | 731 | 876 | 803 | 1373 | 942 | 1289 |
| Modulus of elasticity 5% [MPa] | 0.75 | 0.94 | 0.97 | 1.27 | 0.61 | 0.85 | 1.03 |
| Modulus of elasticity 50% | 0.41 | 0.55 | 0.58 | 0.75 | 0.35 | 0.45 | 0.57 |
| Appearance | nice | nice | nice | nice | nice | nice | nice |
| Odor | no | no | no | no | no | no | no |

| | Composition | | | | | | | |
|---|---|---|---|---|---|---|---|---|
| | Ref1 | Ref2 | Ref3 | Ref4 | Ref5 | Ref6 | Ref7 | Ref8 |
| Polymer P1 | 80.00 | 80.00 | 80.00 | 80.00 | 80.00 | 80.00 | 80.00 | 80.00 |
| Aldimine | R1 | R2 | R3 | R4 | R5 | R6 | R7 | R8 |
| | 8.56 | 8.76 | 8.42 | 9.03 | 9.51 | 4.40 | 5.85 | 6.78 |
| Salicylic acid solution[1] | 1.50 | 1.50 | 1.50 | 1.50 | 0.20 | 1.50 | 1.50 | 1.50 |
| Viscosity (1 d RT) | 50.0 | 50.5 | 35.7 | 22.1 | 28.6 | 36.5 | 43.8 | 39.9 |
| [Pa · s] (7 d 60° C.) | 87.2 | 137.5 | 41.1 | 27.0 | 33.5 | 41.1 | 47.4 | 44.6 |
| Tack-free time | 1 h 10' | 35' | 1 h 30' | 45' | 1 h 22' | 1 h 30' | 2 h | 1 h 35' |
| Tensile strength [MPa] | 2.91 | 3.47 | 2.10 | 1.18 | 1.62 | 1.66 | 1.44 | 0.55 |
| Elongation at break [%] | 508 | 823 | 248 | 1240 | 299 | 936 | 1674 | 1098 |
| Modulus of elasticity 5% [MPa] | 5.66 | 6.72 | 10.30 | 1.02 | 1.61 | 1.00 | 0.79 | 0.41 |
| Modulus of elasticity 50% | 1.82 | 1.70 | 1.81 | 0.54 | 0.95 | 0.51 | 0.40 | 0.17 |
| Appearance | nice | nice | nice | nice | nice | nice | nice | nice |
| Odor | no | no | no | no | no | significant | significant | slight |

[1] 5% in dioctyl adipate
[2] melted at 80° C.

TABLE 2

Composition (in parts by weight) and properties of Z8 to Z11 and Ref9 to Ref13.

| | Composition | | | | | | | | |
|---|---|---|---|---|---|---|---|---|---|
| | Z8 | Z9 | Z10 | Z11 | Ref9 | Ref10 | Ref11 | Ref12 | Ref13 |
| Polymer P2 | 80.00 | 80.00 | 80.00 | 80.00 | 80.00 | 80.00 | 80.00 | 80.00 | 80.00 |
| Aldimine | A1 | A4 | A6 | A7 | R1 | R2 | R3 | R4 | R5 |
| | 7.53 | 7.91 | 6.97 | 8.92 | 7.00 | 7.17 | 6.89 | 7.39 | 7.78 |
| Salicylic acid solution[1] | 1.50 | 1.50 | 1.50 | 1.50 | 1.50 | 1.50 | 1.50 | 0.20 | 0.20 |
| Viscosity (1 d RT) | 16.3 | 24.1 | 24.9 | 16.5 | 19.4 | 27.6 | 23.7 | 27.5 | 27.9 |
| [Pa · s] (7 d 60° C.) | 20.6 | 33.0 | 38.1 | 23.1 | 28.0 | 45.3 | 30.0 | 48.5 | 50.1 |
| Tack-free time | 1 h 35' | 55' | 50' | 50' | 45' | 40' | 2 h 35' | 1 h 20' | 63' |
| Tensile strength [MPa] | 0.52 | 1.05 | 0.66 | 0.65 | 1.22 | 1.72 | 1.79 | 0.66 | 0.92 |
| Elongation at break [%] | 297 | 288 | 241 | 115 | 373 | 346 | 241 | 214 | 211 |
| Modulus of elasticity 5% [MPa] | 0.41 | 0.98 | 0.66 | 0.82 | 1.68 | 3.54 | 4.60 | 0.69 | 1.06 |
| Modulus of elasticity 50% | 0.21 | 0.57 | 0.40 | 0.62 | 0.74 | 1.07 | 1.42 | 0.44 | 0.66 |
| Appearance | nice | nice | nice | nice | nice | nice | nice | nice | nice |
| Odor | no | no | no | no | no | no | no | no | no |

[1] 5% in dioctyl adipate

TABLE 3

Composition (in parts by weight) and properties of Z12 to Z15.

| Composition | Z12 | Z13 | Z14 | Z15 |
|---|---|---|---|---|
| Polymer P3 | 80.00 | 80.00 | 80.00 | 80.00 |
| Aldimine | A1 | A4 | A6 | A7 |
|  | 10.47 | 10.99 | 9.68 | 12.39 |
| Salicylic acid solution[1] | 1.50 | 1.50 | 1.50 | 1.50 |
| Viscosity (1 d RT) [Pa · s] | 15.2 | 14.7 | 13.4 | 15.1 |
| (7 d 60° C.) | 17.5 | 17.5 | 17.3 | 17.5 |
| Tack-free time | 3 h | 2 h 15' | 2 h 5' | 1 h 20' |
| Tensile strength [MPa] | 1.42 | 1.69 | 0.94 | 0.94 |
| Elongation at break [%] | 240 | 263 | 264 | 128 |
| Modulus of elasticity 5% [MPa] | 1.72 | 1.56 | 0.85 | 0.90 |
| Modulus of elasticity 50% | 0.82 | 0.96 | 0.52 | 0.87 |
| Appearance | nice | nice | nice | nice |
| Odor | no | no | no | no |

[1]5% in dioctyl adipate

Compositions Z16 and Ref14

For each composition, the ingredients specified in table 4 were mixed in the amounts specified (in parts by weight) by means of a centrifugal mixer (SpeedMixer™ DAC 150, FlackTek Inc.) with exclusion of moisture at 3000 rpm for one minute and stored with exclusion of moisture. Each composition was tested as follows:

As a measure of plasticizer migration, each composition was applied to a cardboard underlayer such that it had a round base area of diameter 12 mm and a height of 20 mm, and was stored under standard climatic conditions for 7 days. Around each composition, thereafter, a dark oval speck had formed on the cardboard. The dimensions thereof (height and width) were measured and reported in table 4 as Migration.

Composition Z16 is an inventive example. Composition Ref14 is a comparative example.

TABLE 4

Composition (in parts by weight) and properties of Z16 and Ref14.

| Composition | Z16 | Ref14 |
|---|---|---|
| Polymer P4 | 15.00 | 15.00 |
| Chalk[1] | 15.00 | 15.00 |
| Silica[2] | 1.13 | 1.13 |
| Aldimine | A1 | R4 |
|  | 7.80 | 7.65 |
| Dibutyltin dilaurate solution[3] | 1.50 | 1.50 |
| Salicylic acid solution[4] | 3.00 | 3.00 |
| Migration Height | 80 | 110 |
| [mm] Width | 55 | 85 |

[1]ground calcium carbonate coated with fatty acid
[2]hydrophobically modified fumed silica
[3]5% in diisodecyl phthalate
[4]5% in dioctyl adipate Compositions Z17 and Ref 15 and Ref16

These compositions were produced in the same way as described for composition Z16 using the figures in table 5. As a measure of plasticizer migration, each composition was applied to a cardboard underlayer such that it had a round base area of diameter 15 mm and a height of 4 mm, and was stored under standard climatic conditions for 3 months. A dark oval speck formed around each composition on the cardboard, the dimensions of which (height and width) were measured after 7 days and after 3 months under standard climatic conditions and were reported in table 5 as Migration (7 d) or (3 months).

As a measure of the tendency to Stress-cracking on plastic, each composition was applied to a transparent, prestressed plastic sheet of polycarbonate (Makrolon®) having the dimensions of 150×30×2 mm so as to give rise to a coating of 30×30×2 mm in the middle of the stressed sheet. After 24 h under standard climatic conditions, the coating or the composition was removed and the sheet was examined for cracking and other visual changes. The prestressed plastic sheet was fixed in each case to a round piece of timber of diameter 12.5 mm mounted on a board such that the long side was at right angles to the round piece of timber and the narrow end was fixed on the board. "Low" is used to describe the formation of small, slightly visible cracks of length 2 to 3 mm in the edge region of the sheet, which were present only superficially. "Significant" is used to describe a complete crack across the entire width of the sheet which was visible across the entire thickness of the sheet. In addition, very many small cracks were present here in the edge region of the sheet.

Composition Z17 is an inventive example. Compositions Ref15 to Ref16 are comparative examples.

TABLE 5

Composition (in parts by weight) and properties of Z17 and Ref15 to Ref16.

| Composition | | Z17 | Ref15 | Ref16 |
|---|---|---|---|---|
| Polymer P4 | | 15.00 | 15.00 | 15.00 |
| Chalk | | 15.00 | 15.00 | 15.00 |
| Silica | | 1.13 | 1.13 | 1.13 |
| Aldimine | | A1 | R4 | — |
|  | | 5.57 | 5.46 |  |
| Dibutyltin dilaurate solution[1] | | 1.50 | 1.50 | 1.50 |
| Salicylic acid solution[2] | | 3.00 | 3.00 | 3.00 |
| Migration | Height | 18 | 37 | 17 |
| (7 d) [mm] | Width | 19 | 41 | 17 |
| Migration | Height | 23 | 47 | 25 |
| (3 months) [mm] | Width | 23 | 52 | 25 |
| Stress cracking | | low | significant | low |

[1]5% in diisodecyl phthalate
[2]5% in dioctyl adipate

It is clear from the migration results in table 5 that the inventive composition Z17 comprising aldimine A1 has a similar or even lower tendency to plasticizer migration compared to the composition Ref16 without aldimine. By contrast, composition Ref15 comprising aldimine R4, which likewise contains a long-chain substituent and has a similarly high molecular weight to aldimine A1, has significant plasticizer migration.

The invention claimed is:

1. A polyaldimine of the formula (I)

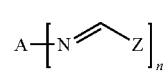

(I)

where n is 2 or 3,

Z is an aryl radical substituted by an alkyl and/or alkoxy group and having a total of 12 to 26 carbon atoms, and A is an n-valent aliphatic or cycloaliphatic hydrocarbyl radical optionally containing ether oxygen and having a molecular weight in the range from 42 to 6'000 g/mol, bonded via at least one tertiary or quaternary carbon atom and/or containing a bi- or tricyclic ring system.

2. A polyaldimine as claimed in claim 1, wherein Z is a radical of the formula (II)

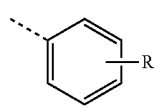
(II)

where R is a linear or branched alkyl radical having 10 to 14 carbon atoms.

3. A polyaldimine as claimed in claim 2, wherein R is branched.

4. A polyaldimine as claimed in claim 3, wherein R is a radical of the formula

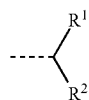

where $R^1$ and $R^2$ are each an alkyl radical and together have 9 to 13 carbon atoms.

5. A polyaldimine as claimed in claim 1, wherein A is selected from the group consisting of 1,2-propylene, 1,3-pentylene, 2-methyl-1,5-pentylene, 2,2(4),4-trimethyl-1,6-hexamethylene, 1,2-cyclohexylene, (1,5,5-trimethylcyclohexan-1-yl)methane-1,3, 4(2)-methyl-1,3-cyclohexylene, methylenedicyclohexan-4-yl, methylenebis(2-methylcyclohexan-4-yl), (bicyclo[2.2.1]heptan-2,5(2,6)-diyl)dimethylene, (tricyclo[5.2.1.0$^{2,6}$]decane-3(4),8(9)-diyl)dimethylene, α,ω-polyoxypropylene having an average molecular weight in the range from 170 to 5'000 g/mol and trimethylolpropane- or glycerol-started tris(ω-polyoxypropylene) having an average molecular weight in the range from 330 to 6'000 g/mol.

6. A reaction product containing at least one polyaldimine as claimed in claim 1, obtained from the reaction of at least one amine of the formula (III) with at least one aldehyde of the formula (IV) in a condensation reaction with release of water, wherein the aldehyde was present stoichiometrically or in a stoichiometric excess in relation to the primary amino groups

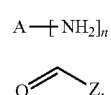
(III)

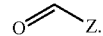
(IV)

7. A mixture of polyaldimines as claimed in claim 1, in which each Z is a radical of the formula (II) and R is selected from linear or particularly branched decyl, undecyl, dodecyl, tridecyl and tetradecyl radicals.

8. A method comprising latently hardening compositions containing isocyanate groups with at least one polyaldimine as claimed in claim 1.

9. The method as claimed in claim 8, wherein some or all of the isocyanate groups are derived from 4,4'- or 2,4'- or 2,2'-diphenylmethane diisocyanate or any mixtures of these isomers.

10. A composition comprising
at least one polyaldimine as claimed in claim 1 and
at least one polyisocyanate and/or at least one polyurethane polymer containing isocyanate groups.

11. The composition as claimed in claim 10, wherein it comprises at least one polyurethane polymer containing isocyanate groups.

12. The composition as claimed in claim 11, wherein some or all of the isocyanate groups are derived from 4,4'- or 2,4'- or 2,2'-diphenylmethane diisocyanate or any mixtures of these isomers.

13. The composition as claimed in claim 10, wherein it additionally comprises at least one further constituent selected from catalysts, fillers, plasticizers and solvents.

14. The composition as claimed in claim 10, wherein it is a one-component composition.

15. The composition as claimed in claim 10, wherein it is an adhesive or a sealant or a coating.

* * * * *